United States Patent [19]
Pannier, Jr. et al.

[11] 3,989,046
[45] Nov. 2, 1976

[54] ASCEPTIC DISPOSABLE RIGID RECEIVER FOR BODY DRAINAGE

[75] Inventors: Karl A. Pannier, Jr.; Gordon S. Reynolds; James L. Sorenson, all of Salt Lake City, Utah

[73] Assignee: Sorenson Research Co., Inc., Salt Lake City, Utah

[22] Filed: Jan. 30, 1975

[21] Appl. No.: 545,376

[52] U.S. Cl. .................. 128/276; 128/DIG. 24; 220/4 R; 220/4 A
[51] Int. Cl.² .......................................... A61M 1/00
[58] Field of Search ........................ 128/275–278, 128/188, 194, DIG. 6, 24; 220/4 B, 4 E, 4 R, 4 A, 4 C; 215/1 C

[56] References Cited
UNITED STATES PATENTS

| | | | |
|---|---|---|---|
| 2,545,577 | 3/1951 | Griffin | 220/4 A |
| 2,752,971 | 7/1956 | Tupper | 220/1 E |
| 3,208,620 | 9/1965 | Herdering | 220/4 E |
| 3,341,048 | 9/1967 | Carbone | 220/4 B |
| 3,646,935 | 3/1972 | Holbrook et al. | 128/276 |
| 3,768,478 | 10/1973 | Fertik et al. | 128/276 |
| 3,843,016 | 10/1974 | Bornhorst et al. | 128/276 |
| 3,878,962 | 4/1975 | Holbrook et al. | 128/276 |

Primary Examiner—Robert W. Michell
Assistant Examiner—Henry S. Layton
Attorney, Agent, or Firm—Hill, Gross, Simpson, Van Santen, Steadman, Chiara & Simpson

[57] ABSTRACT

A self-sustaining rigid body drainage collector including two or more sections each equipped with means for interlocking with another section when snapped together to provide a fluid tight joint; one of said sections having fittings for connection to the patient and to a vacuum line. The collector may be disposed of, empty or full, in an asceptic manner or emptied and reused on the same patient.

8 Claims, 9 Drawing Figures

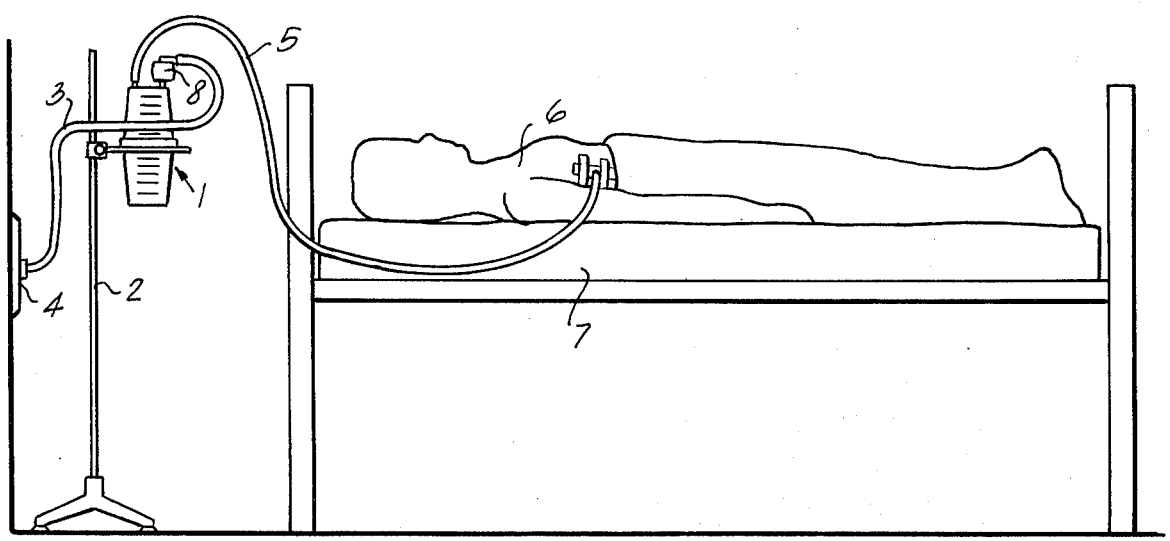
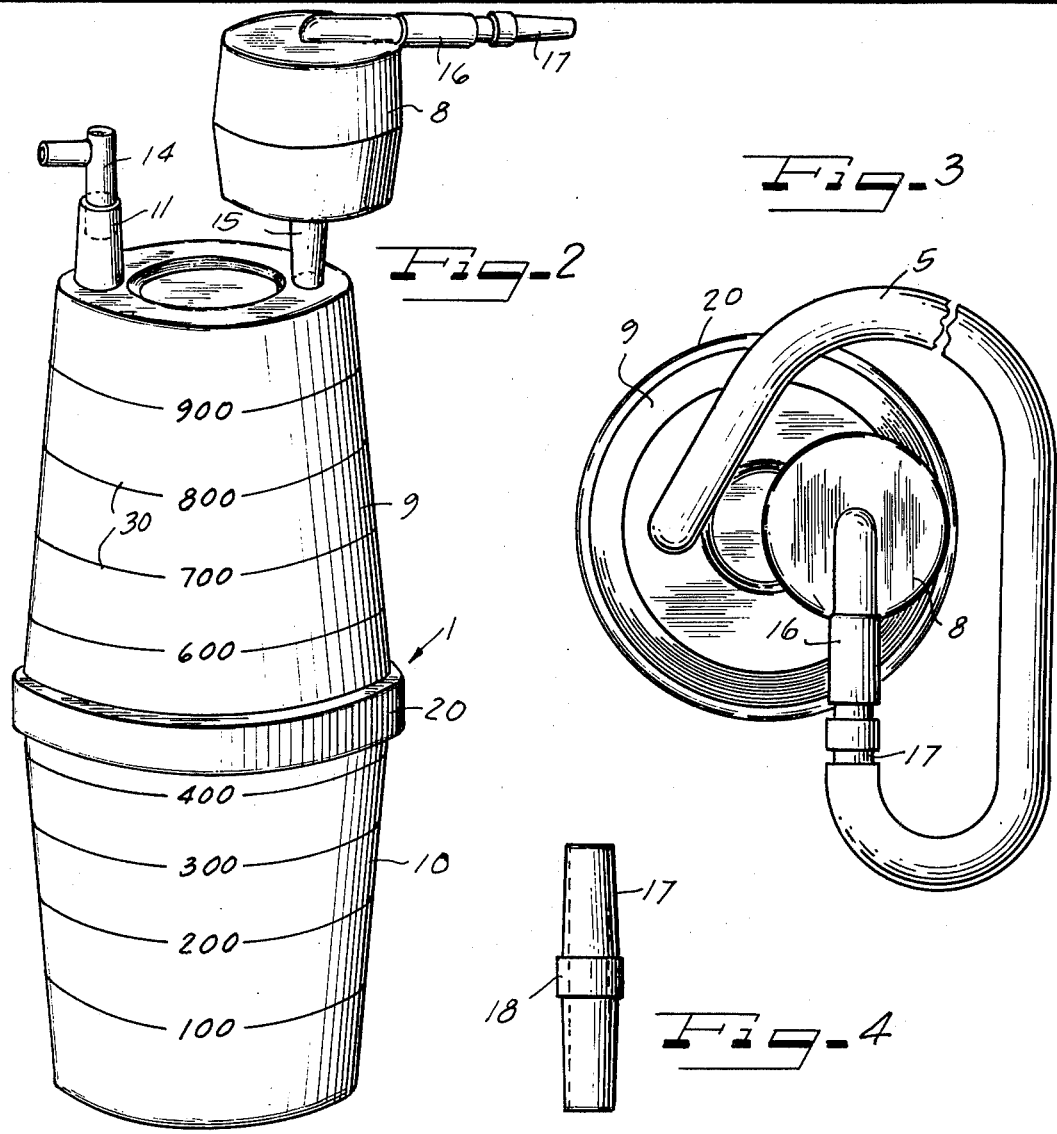

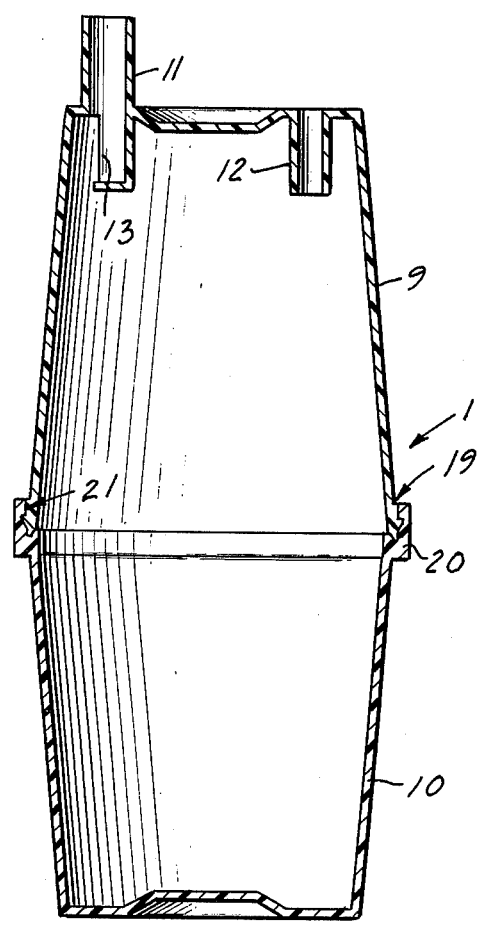
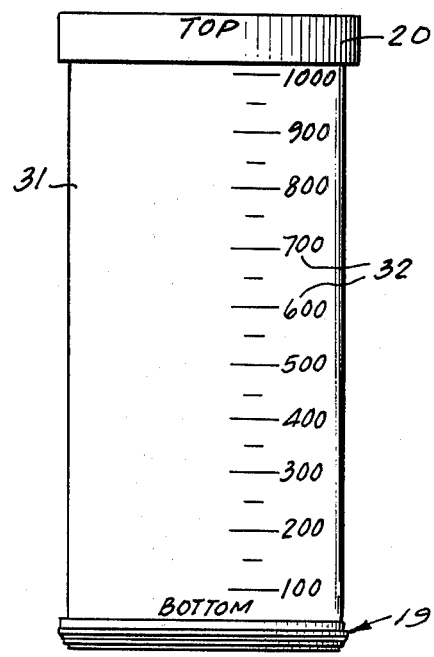
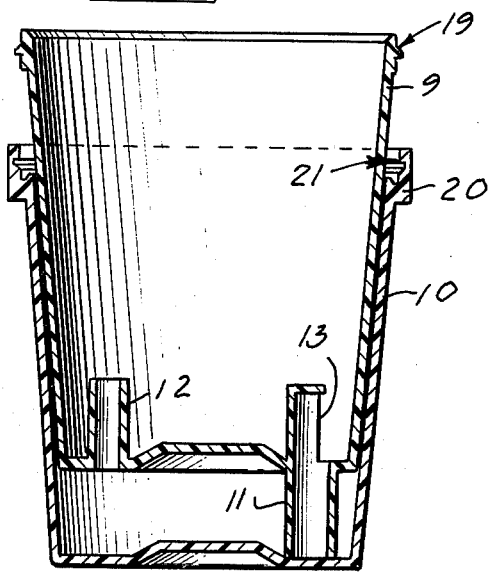
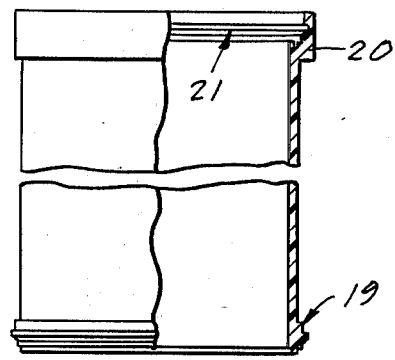
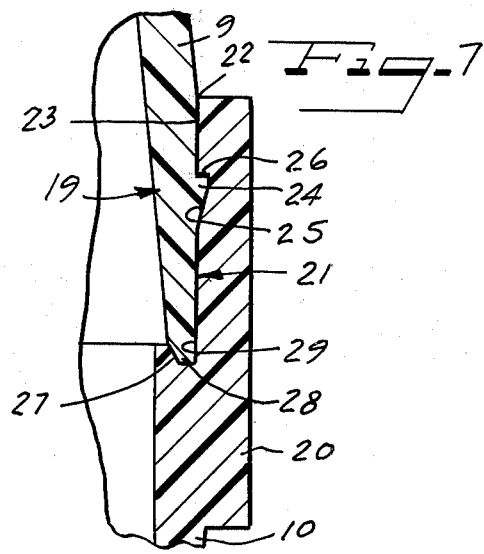

ASCEPTIC DISPOSABLE RIGID RECEIVER FOR BODY DRAINAGE

BRIEF SUMMARY OF THE INVENTION

Heretofore, rigid receptacles for body drainage have been utilized, as well as plastic receptacles which were inserted in a reusable cannister and then disposed of, either full or empty. While these have proved quite satisfactory, some institutions desire a self-sustaining rigid container. Accordingly, it is the object of this invention to provide an economical self-sustaining rigid container that may be asceptically disposed of with or without drainage therein.

The invention comprises upper and lower sections each tapered so that the sections may be nested during shipping and storage for space saving purposes. When assembled, the upper and lower sections taper in opposite directions. The lower section has a closed bottom and open top while the upper section has an open lower end, the upper end being closed except for fittings opening therethrough for connection to a vacuum line and to a patient. The larger ends of each section are provided with an annular arrangement of complemental interlocking parts which, when pressed together, establish a fluid tight seal between the sections, and the sections cannot be separated thereafter without being broken. The drainage receiver may be used with or without a valve to protect the vacuum system from contamination, as may be preferred. The receiver may be emptied, if desired, or disposed of with drainage therein in an asceptic manner. If the valve shows contamination, it may be disposed along with the receiver.

The invention also contemplates the use of an intermediate section equipped to interlock with both the section therebelow and the one thereabove in a fluid tight manner, if an extra large amount of drainage is expected. The parts of the entire apparatus are simple, easy to assemble, and the receiver or collector may be emptied and reused for the same patient.

Many other advantages, features and additional objects of the present invention will become manifest to those versed in the art upon making reference to the description and the accompanying sheets of drawings in which a preferred structural embodiment incorporating the principles of the present invention is shown by way of illustrative example.

BRIEF DESCRIPTION OF THE DRAWINGS

ON THE DRAWINGS:

FIG. 1 is a diagrammatic view of a drainage collector embodying principles of the instant invention shown mounted in operative position and connected to both a vacuum source and a patient;

FIG. 2 is an enlarged view of the assembled device illustrating how a valve may be connected thereto and showing fittings for accommodating both the tubing to the vacuum source and the tubing to the patient;

FIG. 3 is a fragmentary plan view indicating how the device may be disposed as asceptically;

FIG. 4 is a view of a tubular fitting which may be utilized to connect the valve to the vacuum line, or make a connection to the vacuum line without the valve;

FIG. 5 is a vertical sectional view of the device with the upper and lower portions connected;

FIG. 6 is a view of the upper and lower portions in nested relationship as they would be when shipped or stored;

FIG. 7 is a greatly enlarged fragmentary sectional view showing the connection between two sections of the device;

FIG. 8 is an elevational view of an intermediate section which may be disposed between the sections seen in FIG. 5 to enlarge the capacity of the device; and FIG. 9 is a fragmentary part sectional part elevational view of the structure of FIG. 8.

DETAILED DESCRIPTION

In FIG. 1 there is a diagrammatic showing of a drainage receptacle, generally indicated by numeral 1, mounted in operative position upon a stand 2 with a vacuum line 3 leading from the receiver 1 to a plug-in part 4 in the wall which connects with the source of vacuum, as is customary in hospitals and similar institutions. Vacuum line may, of course, lead to some other source of vacuum such as an individual pump, if occasion warrants any such installation.

A tube 5 also leads from the receiver 1 to the body of a patient 6 lying prone upon a bed 7. Drainage from the body of the patient is drawn into the receiver 1 through the line 5 due to suction inside the receiver by way of the line 3. A valve 8 may be interposed between the receiver 1 and the main suction line 3 in order to prevent contamination of the vacuum system in the event the receiver fills beyond a certain point.

Preferably, but not essentially, the valve 8 is like that set forth, described and claimed in our U.S. Pat. No. 3,863,634 entitled, "Asceptic Suction System for Body Fluids and Valve Therefor", and dated Feb. 4, 1975.

In FIGS. 2 and 5, the drainage receptacle 1 is shown assembled. Initially the drainage receptacle is in separate sections, an upper section 9 and a lower section 10. Both sections are tapered, the upper section 9 narrowing upwardly and the lower section 10 narrowing downwardly when assembled so that the assembled structure has somewhat the shape of a barrel. The lower section 10 has a closed bottom and an open top. The upper section 9, when assembled, has an open bottom and a top closed except for two tubes 11 and 12.

The tube 11, which for convenience sake may be termed the patient's tube, extends through the top of the section 9, and inside the top of this section, the tube is substantially half cut away on the side nearest the section wall as indicated at 13 in FIG. 5. This is to guide incoming drainage toward the section wall and the cut of the tube extends substantially flush with the inside of the top of the casing to control splash and foaming, and also to prevent siphoning of drainage back to the patient from the receiver should the collective drainage rise high enough to otherwise effect that result.

One leg of a nipple 14 is inserted in the portion of the tube 11 outside of the casing, and the other leg of that nipple is connected to the patient's line 5 of FIG. 1.

If the valve 8 is utilized in the suction line, a tapered tubular extension 15 providing entrance to the valve and integral with the valve housing is pressed into the tube 12 to mount the valve. At the top thereof, the valve housing is provided with a lateral tube 16 forming an exit opening. If the valve is utilized, a fitting 17 shown in FIG. 4 which is in the form of a tube narrowing externally away from a central cylindrical portion 18, is inserted in one end of the part 16 of the valve and the vacuum tube 3 is pressed over the other end of the fitting.

At the outset, when the receiver is shipped, the upper and lower sections 9 and 10 are nested one within the other as seen in FIG. 6 to save shipping space as well as storage. If so desired, a number of sections for a plurality of receivers may be nested in one stack. A thin sheet of plastic may be used between nested sections in order to facilitate easy removal thereof.

Each of the upper and lower sections 9 and 10 is provided with an annular interlocking arrangement complemental to that of the other section for interlocking engagement. These interlocking arrangements are provided around the large open ends of the sections. In the illustrated instance, the upper section 9 is provided with an annular interlocking arrangement, generally indicated by numeral 19, on the external margin of its open end. The lower section 10 is provided with an annular cylindrical portion at its open end, with an interlocking arrangement, generally indicated by numeral 21, inside that cylindrical portion. These interlocking arrangements could be reversed, that is exchanged one to the other section, if so desired.

With reference more particularly to FIG. 7, it will be seen that the taper of the upper section 9 allows its entry into the cylindrical portion 20 of the lower section. The taper of the arrangement 19 terminates exteriorly at the point 22 to slightly overlap the upper edge of the cylindrical portion 20 of the lower section. Then the upper section is preferably straight as at 23 for intimate face-to-face engagement with the upper portion 20 on the lower section. This straight portion on the upper section includes an outstanding annular detent 24 which functions like a hook and seats in a complemental recess 25 in the portion 20, the top of the detent 24 being flat to abut a flat shoulder at the top of the recess, as indicated at 26. The lower end of the part 19 is chamfered in the inside as indicated at 27 to form a narrow projection 28 to seat in a groove 29 formed in the part 20 of the lower section. Therefore, when the sections are united, there is a point of seal at 22, a positive seal at 26, and a seal in the groove 29.

While the sections 9 and 10 are molded with sufficient rigidity to be self-sustaining, there is enough resiliency to permit the upper portion 9 to be snapped at its open end into the cylindrical portion 20 of the lower section 10. Consequently, when the device is put to use, it is a simple expedient to separate the nested sections, invert the upper section, and snap the two sections together forming a positive fluid and airtight seal therebetween, which cannot be separated except by breakage. The connections to the patient and vacuum line are then made and the receiver 1 put to use.

When drainage of the particular patient is completed, the receiver 1 may be disposed of with the drainage contents therein by means consistent with local hospital practice. If it is to be disposed of asceptically, it is a simple expedient to remove the connections to the vacuum line, and connect all or a portion of the patient line to the fitting 17. If the valve is contaminated, it remains in place and is disposed of with the receiver 1 as illustrated in FIG. 3. However, if the valve is not contaminated, it should not be disposed of, but the fitting 17 can be removed and pressed in to the tube 12 and for asceptic disposal a portion or all of the patient's tube may be connected to the protruding part of the fitting. If so desired, the receptacle may be emptied through the patient tube 11 and discarded with other dry refuse. In cases where prolonged suction is required by a particular patient, the receptacle can be disconnected, the contents emptied and the receptacle returned for reuse by that same patient. Consequently, the receptacle meets the requirements or practice of substantially any hospital or similar institution.

The sections of the receptacle are preferably provided with indicating indicia 30 as seen in FIG. 2 and the sections are preferably transparent.

If a great amount of drainage is expected from a patient and several connections are not advisable, a central section may be added to the receptacle, as seen in FIGS. 8 and 9. The central section is provided at the bottom with the interlocking arrangement 19 like the upper section 9, and at the top with a cylindrical portion 20 and interlocking arrangement 21, the same as the lower section 10. While this intermediate section 31 is also transparent and is provided with indicia 32, compensation must be made for the amount in the intermediate section in addition to the amount shown on the upper and lower sections 9 and 10. Accordingly, the invention is extremely versatile in its usage.

The claims are:

1. A self-sustaining body drainage receiver having tubular fittings in the top thereof for connection to the body of a patient and to a vacuum source, wherein the improvement comprises said receiver initially being in separate upper and lower generally cup-shaped sections each of which has therein a receiving chamber space adapted to complement the chamber space of the other section to provide a combined receiving chamber intended to contain body drainage, and each of said sections having a large open end, adapted to be assembled endwise with the open end of the other section, and annular interlocking means around the margin of the open end of each said section complemental to the interlocking means of the other section, said means being adapted to be snapped together when said open ends are assembled to thereby provide an inseparable fluid tight seal and form the complete receiver from which the sections cannot be separated without breakage.

2. The drainage receiver of claim 1 wherein said receiver sections are substantially the same size.

3. The drainage receiver of claim 1 wherein the upper receiver section tapers inwardly and upwardly, and the lower section tapers inwardly and downwardly giving the receiver substantially a barrel shape when the sections are joined.

4. The drainage receiver of claim 1 wherein the upper receiver section contains said tubular elements, and the tube for connection to the vacuum line terminates even with the top face of said upper section to receive a fitting for a vacuum tube or an intake for a valve in the vacuum tube line.

5. The drainage receiver of claim 1 wherein when connections are removed the receiver may be emptied through the tube connected to the patient with air entering through the tube connected to the vacuum source.

6. The drainage receiver of claim 1 wherein the large end of one of said sections is enlarged to receive the large end of the other section, said one section having its interlocking means on the inside face of its large end, and said other section having its complemental interlocking means on the outside margin of its large end.

7. The drainage receiver of claim 6, including
an annular recess having a straight lateral termination at one end and an annular groove spaced therefrom in the enlarged end of said one section,
an annular detent on said other section to fit in said recess for hook-like engagement with said straight lateral termination, and
the end of said other section being narrowed to fit intimately into said groove.

8. The drainage receiver of claim 1 including
an intermediate section to enlarge the capacity of said receiver,
interlocking means on the end of said intermediate section complemental to the means at the top end of said lower section, and
an interlocking means on the top end of said intermediate section complemental to the means at the lower end of said upper section.

* * * * *